US00PP35091P2

(12) United States Plant Patent
Bourne

(10) Patent No.: US PP35,091 P2
(45) Date of Patent: Apr. 11, 2023

(54) GRAPEVINE NAMED 'SV35-210-349'

(50) Latin Name: ***Vitis vinifera* L.**
Varietal Denomination: SV35-210-349

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 17/803,352

(22) Filed: May 26, 2022

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 6/88
See application file for complete search history.

*Primary Examiner* — Anne Marie Grunberg
(74) *Attorney, Agent, or Firm* — Eric C. Cole; Baker Manock & Jensen, PC

(57) ABSTRACT

A new and distinct variety of grapevine plant named 'SV35-210-349' particularly characterized by its very large, very crisp yellow green colored berries that have a neutral flavor that is characteristic of *Vitis vinifera* and which ripen in late September to early October in the McFarland, Calif. area.

3 Drawing Sheets

Scientific name of the genus and species of the plant claimed: The plant claimed relates to a new and distinct variety of *Vitis vinifera* L.

Variety denomination: The plant claimed shall be known as 'SV35-210-349'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV35-210-349'. As used herein, 'grapevine' refers to all plant parts including, vines, canes, tendrils, leaves, fruit and roots of 'SV35-210-349'. Grapevine named 'SV35-210-349' is the result of an effort to produce a late-ripening, white seedless table grape with fruit characteristics superior to currently available commercial cultivar 'Autumn King' (U.S. Plant Pat. No. 16,284). This new grapevine originated from a cross conducted in May 2014 near McFarland, Calif. between female parent grapevine selection 'SV30-23-590' (unpatented) and male parent grapevine cultivar 'SV22-104e-84' (U.S. Plant Pat. No. 28,833). Resultant ovules from the cross were harvested 42 days after pollination and cultured on 'McCown's Woody Plant Medium'. Subsequently, the resultant embryonic plants were cultured in the same medium in the laboratory under twelve hours of light from standard fluorescent lamps at 29° C. The seedlings from this effort were transplanted to the greenhouse in November of 2014 and grown in the greenhouse at 29° C. with 12 hours illumination under high pressure sodium vapor lamps. The seedling population of 473 plants was planted in the field in the spring of 2015 near Delano, Calif. The new grapevine was selected from this seedling population on Oct. 5, 2017. It was then propagated by cuttings and grafted to 'Freedom' (unpatented) rootstock in 2018. The present invention has been found to retain its distinctive characteristics through two successive asexual propagations in 2019 and 2020 near Delano, Calif.

Grapevine named 'SV35-210-349' differs from its female parent grapevine 'SV30-23-590' (unpatented) by having fruit that ripens in late September to early October while grapevine 'SV30-23-590' (unpatented) fruit ripens in August. Grapevine named 'SV35-210-349' has fruit with small, soft seed traces that are not noticeable when eating while the seed traces of grapevine 'SV30-23-590' (unpatented) are large and partially lignified.

Grapevine named 'SV35-210-349' differs from its male parent 'SV22-104e-84' (U.S. Plant Pat. No. 28,833) by having much larger berries, 8 grams for grapevine named 'SV35-210-349' versus 5.6 grams 'SV22-104e-84' (U.S. Plant Pat. No. 28,833), and more compact clusters for grapevine named 'SV35-210-349'.

Grapevine named 'SV35-210-349' most closely resembles commercially available grapevine named 'Autumn King' (U.S. Plant Pat. No. 16,284) from which it may be distinguished by its smaller berry size, 8 grams for grapevine named 'SV35-210-349' versus 9.8 grams for grapevine named 'Autumn King' (U.S. Plant Pat. No. 16,284). The fruit clusters of grapevine named 'SV35-210-349' are compact while the fruit clusters of grapevine named 'Autumn King' (U.S. Plant Pat. No. 16,284) are loose.

SUMMARY OF THE INVENTION

The following are the most outstanding and distinguishing characteristics of this new variety when grown under normal horticultural practices near McFarland, Calif.:

1. Very large, sweet berries with neutral flavor;
2. Very crisp berry texture; and
3. Small fruit clusters.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken from a plant about 5 years-old, grown in a field near McFarland, Calif. in 2021.

DETAILED BOTANICAL DESCRIPTION

Figure 1:
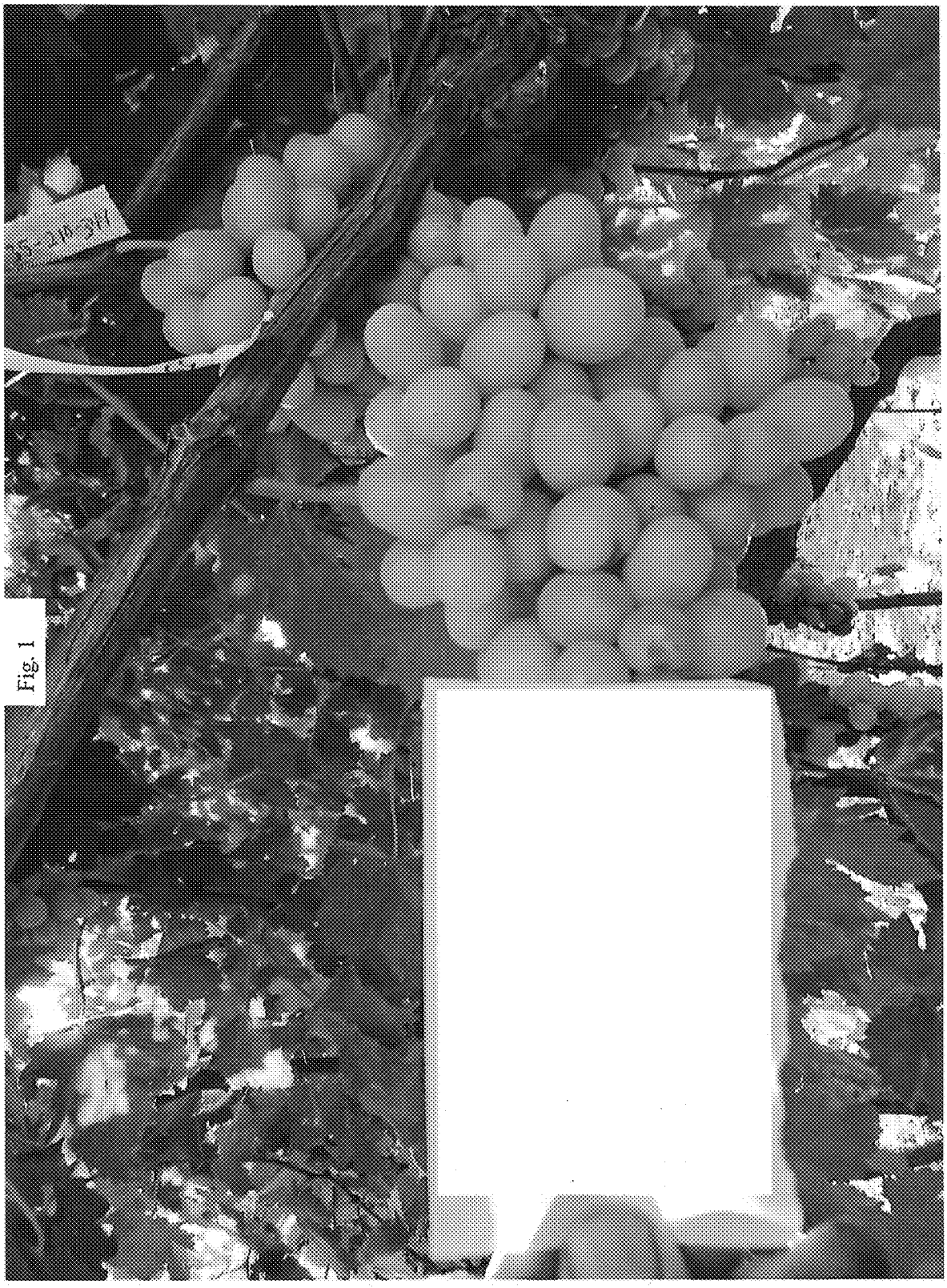
FIG. 1 Seedling vine with fruit clusters.
Figure 2:
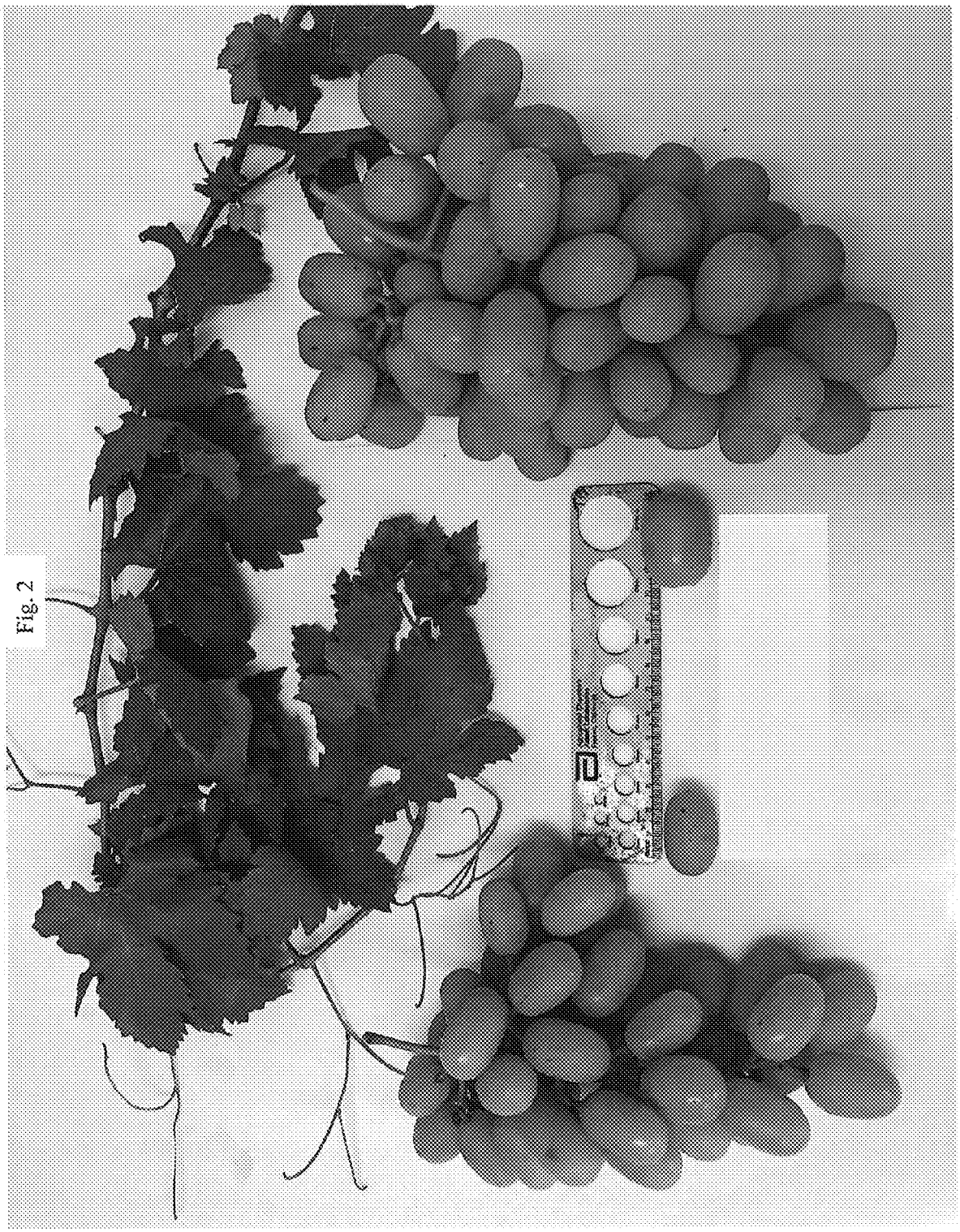
FIG. 2 Fruit cluster natural (at left) and fruit cluster treated with gibberellic acid and trunk girdling (at right) with green shoot bearing leaves and tendrils.
Figure 3:
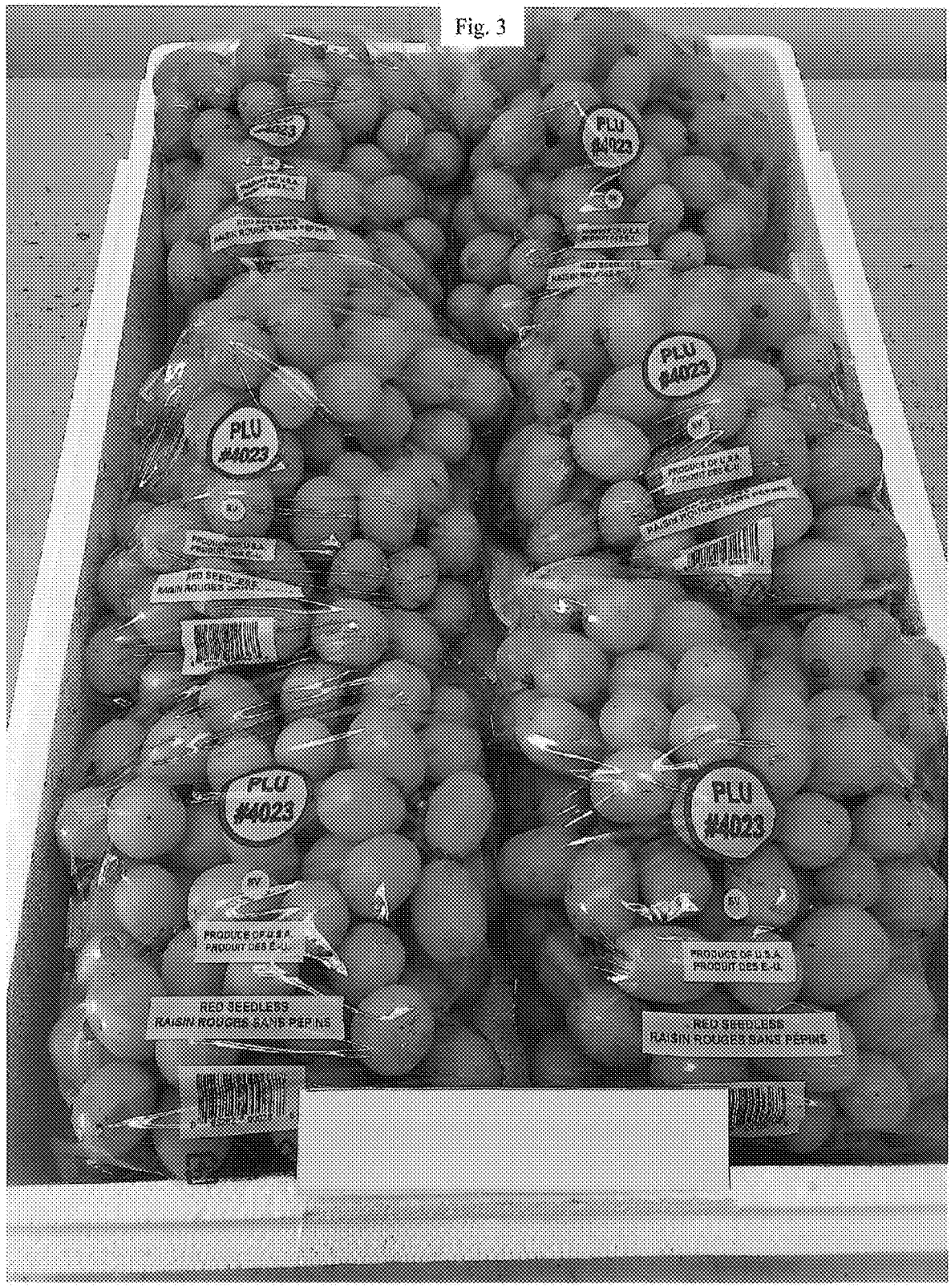
FIG. 3 Fruit clusters packaged for cold storage and shipping test.

The following detailed description sets forth the distinctive characteristics of grapevine named 'SV35-210-349'. Descriptions of the new invention apply to vines of grapevine named 'SV35-210-349' grown on 'Freedom' (unpatented) rootstock at a density of 1,537 vines per hectare grown near McFarland, Calif. in 2021. These vines were in their third year of production having been planted in 2018. These descriptions are believed to apply generally to the new variety grown under similar circumstances elsewhere. Variation due to soil and climatic conditions in other locations may be seen. References to color correspond to The Royal Horticultural Society's Colour Chart, The Royal Horticultural Society, London, United Kingdom, 1966, 1986, 1995, 2001. Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis* spp.) (Anonymous, International Plant Genetic Resources Institute, 1997, ISBN 92-9043-352-3).

Classification:

*Family*.—Vitaceae.
*Botanical name*.—*Vitis vinifera* L.
*Variety name*.—'SV35-210-349'.

Plant:

*Vigor*.—Vigorous; vines spur-pruned and shoot thinned to 32 shoots producing 261 cm of growth per cane.
*Density of foliage*.—Dense.
*Productivity*.—Very productive when spur pruned, up to 38,608 kg/hectare.
*Hardiness*.—Hardiness observed to 0° C.
*Rootstock*.—'Freedom' (unpatented).

Trunk:

*Shape*.—Broadly elliptical.
*Straps*.—Long, split.
*Surface texture*.—Shaggy.
*Trunk circumference*.—25.4 cm at 1.0 m of height.
*Inner bark color*.—RHS Greyed orange group 174B.
*Outer bark color*.—RHS Greyed orange group 177B.

Mature leaves:

*Average blade length*.—14.2 cm.
*Average blade width*.—16.9 cm.
*Size of blade*.—Large.
*Number of lobes*.—5.
*Shape*.—Pentagonal.
*Anthocyanin coloration of main veins on the upper side of the blade*.—Absent.
*Mature leaf profile*.—Cupped upwards around entire margin.
*Blistering* (*upper surface*).—Absent.
*Leaf blade tip*.—In plane of blade.
*Margins*.—Lobed, serrated, undulating.
*Apex*.—Broadly acuminate.
*Bases*.—Sagittate.
*Thickness*.—Medium.
*Undulation of blade between main and lateral veins*.—Slight.
*Shape of teeth*.—Broadly conical, both sides convex.
*Length of teeth*.—0.5 mm to 1.5 mm; average 0.7 mm.
*Width of teeth*.—0.7 mm to 1.1 mm; average 0.9 mm.
*Ratio length/width of teeth*.—About 7:9.
*General shape of petiole sinus*.—Wide open.
*Tooth at petiole sinus*.—Absent.
*Petiole sinus limited by veins*.—Absent.
*Shape of upper lateral sinus*.—Open.
*Depth of upper lateral sinus*.—Shallow; about 2 cm.
*Prostrate hairs between veins* (*lower surface*).—Absent.
*Erect hairs between veins* (*lower surface*).—Absent.
*Prostrate hairs on main veins* (*lower surface*).—Very sparse.
*Density of erect hairs on main veins* (*lower surface*).—Very sparse.
*Prostrate hairs on main veins* (*upper surface*).—Very sparse.
*Upper surface*.—Summer color: RHS Green group 137C. Autumn color: RHS Yellow group 11B. Surface texture: Rough. Surface appearance: Shiny. Goffering of blade: Absent.
*Lower surface*.—Summer color: RHS Yellow green group 146B. Anthocyanin coloration of main veins on lower leaf surface: Absent. Glossiness: Low. Pubescence distal portion of surface: Absent. Surface texture: Rough. Surface appearance: Dull.
*Petiole*.—Length: 13.1 cm. Length of petiole compared to middle vein: About equal. Density of prostrate hairs: Very sparse. Density of erect hairs: Sparse. Shape of base of petiole sinus: Wide open. Color: In shade: RHS Yellow Green group 145C. In sun: RHS Yellow Green group 145B.

Tendrils:

*Number*.—Bifurcated and trifurcated; forming irregularly above node 4.
*Length*.—7.1 cm to 24.3 cm; average about 14.3 cm.
*Diameter*.—0.2 mm.
*Texture*.—Smooth.
*Color*.—RHS Yellow Green group 149B.

Growing tips:

*Color*.—RHS Yellow green group 144B.
*Anthocyanins*.—Absent.
*Shape*.—Flattened.
*Apex*.—Fully open.
*Prostrate hair on tips*.—Absent, young developing leaves have abundant prostrate hairs.
*Anthocyanin coloration of prostrate hairs on tips*.—Absent.
*Erect hairs on tip*.—Absent.

Young shoots:

*Shoot attitude*.—Erect.

*Color of dorsal side of internode*.—RHS Yellow Green group 144B.

*Color of ventral side of internode*.—RHS Yellow Green group 145B.

*Color of dorsal side of nodes*.—RHS Yellow Green group 144B with Red purple 59B. developing in cool temperatures.

*Color of ventral side of nodes*.—RHS Yellow Green group 145A.

*Erect hairs on internodes*.—Absent.

*Prostrate hairs on internodes*.—Sparse.

Woody shoot:

*Canes*.—Shape: Broadly elliptical. Internode length: About 12.1 cm. Width at node: 12.6 mm. Surface: Smooth. Main color: RHS Greyed Orange group 172A. Lenticels: Inconspicuous.

*Buds*.—Shape: Slightly pointed. Cane bud fruitfulness: Basal buds fruitful, usually 2 clusters per shoot. Length: 6 mm. Width: 7 mm. Height: 5 mm. Color: RHS Greyed orange group 166B.

Flowers:

*Flower sex*.—Perfect.

*Position of first flowering nodes*.—Third node.

*Number of inflorescences per shoot*.—1 or 2.

*Calyptra color*.—RHS Yellow green group 144A.

*Ovary length*.—2 mm.

*Ovary width*.—1 mm.

*Ovary color*.—RHS Green group 143A.

*Filament length*.—3 mm.

*Filament color*.—Translucent, absence of pigmentation.

*Anther length*.—1 mm.

*Anther color*.—RHS Yellow group 8C.

*Date of full bloom*.—May 10, 2022 near McFarland, Calif.

Fruit:

*Ripening period*.—Late season at McFarland, Calif.

*Date of ripening*.—Sep. 27, 2021 at McFarland, Calif.

*Use*.—Fresh market.

*Keeping quality*.—Very good.

*Shipping quality*.—Very good.

*Solids-sugar*.—18.5 brix at full maturity.

*Total acidity*.—0.36.

*Juice*.—pH: 3.9.

*Bunch*.—Size: Small. Length (peduncle excluded): About 19.3 cm. Width: About 15.5 cm. Weight: Natural, without gibberellic acid treatment: 602 g. With gibberellic acid treatment: 785 g. Density: Slightly compact. Number of berries: 65. Form: Conical.

*Peduncle*.—Length: About 4.6 cm. Lignification: Slight. Color: RHS Yellow green group 144B.

*Berry*.—Size: Large. Uniformity of size: Uniform. Weight Natural, without gibberellic acid treatment: 8.0 g. With gibberellic acid treatment: 11.8 g. Shape: Natural, without gibberellic acid treatment: Elliptic. With gibberellic acid treatment: Elliptic. Presence of seeds: Seedless; most berries develop one or two small, soft rudimentary seeds less than 1.0 mm in length. Cross section: Circular. Dimensions: Longitudinal axis: About 3.2 cm at base. Horizontal axis: About 2.5 cm. Skin color (without bloom): RHS Yellow Green group 144C. Coloration of flesh: Translucent. Juiciness of flesh: Very juicy. Juice color: RHS Yellow green group 148D. Berry firmness: Very firm. Particular flavor: Neutral, typical *Vitis vinifera*. Bloom (cuticular wax): Strong. Pedicel length: 1.1 cm. Berry separation from pedicel: With difficulty; vascular traces well-developed.

*Skin*.—Thickness: Medium. Texture: Crisp. Reticulation: Absent. Roughness: Absent. Tenacity: Tenacious to flesh.

*Tendency to crack*.—Resistant.

Disease and insect resistance: No particular resistance or susceptibility has been observed. Normal disease control practices can be used.

Having thus described and illustrated our new variety of grapevine, we claim:

1. A new and distinct variety of grapevine plant named 'SV35-210-349', substantially as illustrated and described herein.

* * * * *